(12) United States Patent
Liu et al.

(10) Patent No.: US 12,391,744 B1
(45) Date of Patent: Aug. 19, 2025

(54) MICROMOLECULAR TYPE III COLLAGEN PEPTIDE CAPABLE OF PROMOTING SECRETION OF TYPE III AND IV COLLAGENS, AND PREPARATION METHOD THEREFOR

(71) Applicant: BEIJING SEMNL BIOTECHNOLOGY CO., LTD., Beijing (CN)

(72) Inventors: Aiqing Liu, Beijing (CN); Jingqi Liu, Beijing (CN); Haiyan Wang, Beijing (CN); Mingkang Lei, Beijing (CN); Xiaoqing Zhang, Beijing (CN); Shuang Liu, Beijing (CN); Pengcheng Li, Beijing (CN); Xinyu Ma, Beijing (CN)

(73) Assignee: BEIJING SEMNL BIOTECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/810,577

(22) Filed: Aug. 21, 2024

(30) Foreign Application Priority Data

Feb. 19, 2024 (CN) .................. 202410182043.X

(51) Int. Cl.
*C07K 14/78* (2006.01)
*C07K 1/34* (2006.01)

(52) U.S. Cl.
CPC ............... *C07K 14/78* (2013.01); *C07K 1/34* (2013.01)

(58) Field of Classification Search
None
See application file for complete search history.

(56) References Cited

FOREIGN PATENT DOCUMENTS

| CN | 104140992 A | 11/2014 |
|---|---|---|
| CN | 108103131 A | 6/2018 |
| CN | 111574617 A | 8/2020 |
| CN | 111944866 A | 11/2020 |
| CN | 114015739 A | 2/2022 |
| CN | 114032269 A | 2/2022 |
| CN | 116179634 A | 5/2023 |
| CN | 116463388 A | 7/2023 |
| JP | 2003238597 A | 8/2003 |
| KR | 20030074577 A | 9/2003 |
| KR | 20090106807 A | 10/2009 |

OTHER PUBLICATIONS

Yan Jin et al., Screening and identification of DPP-IV inhibitory peptides from deer skin hydrolysates by an integrated approach of LC-MS/MS and in silico analysis, Journal of Functional Foods, 2015, pp. 344-357, vol. 18.
Oligopeptides powder of marine fish, GB/T 22729-2008, National standards of the People's Republic of China, Dec. 31, 2008.
First Office Action of counterpart Chinese Patent Application No. 202410182043.X issued on Mar. 27, 2024.
First Search report of counterpart Chinese Patent Application No. 202410182043.X issued on Mar. 22, 2024.
Second Office Action of counterpart Chinese Patent Application No. 202410182043.X issued on Apr. 25, 2024.
Notice of Allowance of counterpart Chinese Patent Application No. 202410182043.X issued on May 9, 2024.
Supplementary Search report of counterpart Chinese Patent Application No. 202410182043.X issued on May 6, 2024.

*Primary Examiner* — Anand U Desai

(57) ABSTRACT

The present disclosure provides a micromolecular type III collagen peptide capable of promoting secretion of type III and IV collagens, and a preparation method therefor, belonging to the field of micromolecular peptides. The method for preparing the micromolecular type III collagen peptide comprises the steps of pretreating livestock and poultry skin, enzymatically hydrolyzing the livestock and poultry skin by using a combined enzyme and the like. The micromolecular type III collagen peptide may include any one or more of amino acid sequences shown in SEQ ID NOs. 1-8. The preparation method of the present disclosure has short production period. The resulting product has good color and smell, high recovery rate, high content of the micromolecular type III collagen peptide and a specific sequence.

6 Claims, 6 Drawing Sheets

Specification includes a Sequence Listing.

SEQUENCE LISTING

```
Sequence total quantity: 16
SEQ ID NO: 1            moltype = AA  length = 21
FEATURE                 Location/Qualifiers
source                  1..21
                        mol_type = protein
                        organism = synthetic construct
SITE                    3
                        note = HYP
SITE                    12
                        note = HYP
SITE                    15
                        note = HYP
SEQUENCE: 1
GQXGDKGEGG AXGVXGIAGP R                                                   21

SEQ ID NO: 2            moltype = AA  length = 15
FEATURE                 Location/Qualifiers
source                  1..15
                        mol_type = protein
                        organism = synthetic construct
SITE                    9
                        note = HYP
SEQUENCE: 2
GERGEAGSXG IAGPK                                                          15

SEQ ID NO: 3            moltype = AA  length = 18
FEATURE                 Location/Qualifiers
source                  1..18
```

```
                              mol_type = protein
                              organism = synthetic construct
SITE                          6
                              note = HYP
SITE                          9
                              note = HYP
SEQUENCE: 3
GERGGXGGXG PQGPAGKN                                                    18

SEQ ID NO: 4                  moltype = AA  length = 12
FEATURE                       Location/Qualifiers
source                        1..12
                              mol_type = protein
                              organism = synthetic construct
SITE                          6
                              note = HYP
SEQUENCE: 4
GEAGSXGIAG PK                                                          12

SEQ ID NO: 5                  moltype = AA  length = 15
FEATURE                       Location/Qualifiers
source                        1..15
                              mol_type = protein
                              organism = synthetic construct
SITE                          6
                              note = HYP
SITE                          9
                              note = HYP
SEQUENCE: 5
GEGGAXGVXG IAGPR                                                       15

SEQ ID NO: 6                  moltype = AA  length = 18
FEATURE                       Location/Qualifiers
source                        1..18
                              mol_type = protein
                              organism = synthetic construct
SITE                          6
                              note = HYP
SITE                          12
                              note = HYP
SEQUENCE: 6
GENGIXGENG AXGPMGPR                                                    18

SEQ ID NO: 7                  moltype = AA  length = 18
FEATURE                       Location/Qualifiers
source                        1..18
                              mol_type = protein
                              organism = synthetic construct
SITE                          14..15
                              note = HYP
SEQUENCE: 7
GPAGANGLPG EKGXXGER                                                    18

SEQ ID NO: 8                  moltype = AA  length = 15
FEATURE                       Location/Qualifiers
source                        1..15
                              mol_type = protein
                              organism = synthetic construct
SITE                          6
                              note = HYP
SITE                          9
                              note = HYP
SEQUENCE: 8
GEGGAXGVXG IAGPR                                                       15

SEQ ID NO: 9                  moltype = DNA  length = 20
FEATURE                       Location/Qualifiers
source                        1..20
                              mol_type = other DNA
                              organism = synthetic construct
SEQUENCE: 9
ccctcccaca actctgacat                                                  20

SEQ ID NO: 10                 moltype = DNA  length = 21
FEATURE                       Location/Qualifiers
source                        1..21
                              mol_type = other DNA
                              organism = synthetic construct
SEQUENCE: 10
```

```
agggaatcgc gtttataggg t                                                     21

SEQ ID NO: 11           moltype = DNA   length = 22
FEATURE                 Location/Qualifiers
source                  1..22
                        mol_type = other DNA
                        organism = synthetic construct
SEQUENCE: 11
tggtctgcaa ggaatgcctg ga                                                    22

SEQ ID NO: 12           moltype = DNA   length = 22
FEATURE                 Location/Qualifiers
source                  1..22
                        mol_type = other DNA
                        organism = synthetic construct
SEQUENCE: 12
tctttccctg ggacaccatc ag                                                    22

SEQ ID NO: 13           moltype = DNA   length = 21
FEATURE                 Location/Qualifiers
source                  1..21
                        mol_type = other DNA
                        organism = synthetic construct
SEQUENCE: 13
tccagggttt ccaggcgact c                                                     21

SEQ ID NO: 14           moltype = DNA   length = 23
FEATURE                 Location/Qualifiers
source                  1..23
                        mol_type = other DNA
                        organism = synthetic construct
SEQUENCE: 14
ggtcccgtgc caataacagt tcc                                                   23

SEQ ID NO: 15           moltype = DNA   length = 20
FEATURE                 Location/Qualifiers
source                  1..20
                        mol_type = other DNA
                        organism = synthetic construct
SEQUENCE: 15
cttaagggtt gcttgcttgc                                                       20

SEQ ID NO: 16           moltype = DNA   length = 20
FEATURE                 Location/Qualifiers
source                  1..20
                        mol_type = other DNA
                        organism = synthetic construct
SEQUENCE: 16
gttcgtggga gatgaaggaa                                                       20
```

MICROMOLECULAR TYPE III COLLAGEN PEPTIDE CAPABLE OF PROMOTING SECRETION OF TYPE III AND IV COLLAGENS, AND PREPARATION METHOD THEREFOR

CROSS-REFERENCE TO RELATED APPLICATION

The present application claims priority from Chinese Patent Application No. 202410182043.X filed on Feb. 19, 2024, the contents of which are incorporated herein by reference in their entirety.

REFERENCE TO SEQUENCE LISTING

This application includes a Sequence Listing filed electronically as an XML file named "Sequence listing_ERICL-24003-USPT.xml", created on Aug. 15, 2024, with a size of 20,214 bytes. The Sequence Listing is incorporated herein by reference.

TECHNICAL FIELD

The present disclosure belongs to the field of micromolecular peptides and particularly provides a micromolecular type III collagen peptide capable of promoting secretion of type III and IV collagens and a preparation method therefor.

BACKGROUND

Type III type I collagens mainly present in the skin of infants and a main structural component of hollow organs such as large blood vessels, uterus, intestinal tracts and the like, and maintains the morphology and structure of skin, tissues and organs as an extracellular matrix protein. The type III collagen further interacts with platelets in a coagulation cascade reaction and is also an important signal molecule for wound healing. The type III collagen fiber is fine and used for supporting the softness and tenderness of the skin, and enables the skin to be delicate and fully elastic. The higher content of the type III collagen enables the skin to be more delicate and tender. The type III collagen can better recover the wound after trauma, such that scars are not easy to remain.

The currently marketed orally taken products are mainly type I collagen peptide and type I collagen peptide. For example, Chinese patent with the publication number CN116463388A discloses a method for extracting a hydrolyzed type I collagen peptide powder. The extraction method comprises the steps of pretreatment, degreasing treatment, enzymolysis, isoelectric precipitation and purification. The method effectively improves the hydrolysis degree and the hydroxyproline extraction rate. The prepared type I collagen has an isoelectric point which can be adjusted within a range of 4.4-6.2, such that the collagen has a triple helix structure. The prepared hydrolyzed type I collagen has higher contents of proteins and chondroitin sulfate (dry basis), and lower crude fat content. Chinese patent with the publication number CN104140992A discloses a large-scale method for preparing a fish scale type I collagen peptide. Marine fish scales or freshwater fish scales are used as raw materials and subjected to alkali and acid pretreatment, the impurities are removed, type I collagen in the fish scales is directly enzymatically hydrolyzed in a directional manner into a type I collagen peptide with the concentrated molecular weight distribution, then the directional enzymatic hydrolysate is separated, purified and concentrated at normal temperature by using a continuous centrifugal separation and membrane separation technology to obtain a fish scale type I collagen peptide solution with the purity of ≥95% and the molecular weight of 1,000 daltons or lower, and finally, a finished product is rapidly dried by using a spray-drying technology. The method has a simple and feasible process, and short production period, and is highly efficient, energy-saving and suitable for large-scale production. The produced fish scale type I collagen peptide product has high purity and good quality. The content of the peptide with the molecular weight less than 1,000 daltons reaches 97% or greater.

A recombinant human type III type I collagens mostly externally used in the cosmetic medicine industry, but an oral type III collagen peptide product does not appear yet and a space is left for further researching a preparation method therefor.

SUMMARY

In order to solve the above problems, the present disclosure aims to prepare an oral polypeptide product containing a specific sequence of a micromolecular type III collagen peptide, which contains a micromolecular type III collagen peptide capable of promoting secretion of type III and IV collagens.

Specifically, the present disclosure provides a method for preparing a micromolecular type III collagen peptide.

The preparation method comprises the following steps:
(1) pretreating livestock and poultry skin, sequentially comprising: first water washing, sodium chloride solution soaking, sodium hydroxide solution soaking and second water washing, wherein the pH value and the electrical conductivity in the second water washing are adjusted;
(2) enzymatically hydrolyzing the livestock and poultry skin treated in step (1) by using a combined enzyme, and filtering an enzymatic hydrolysate to obtain a clear liquid;
(3) decoloring and filtering the clear liquid obtained in step (2), exchanging water until the solid matters is 0, and performing nanofiltration to obtain a high-concentration solution;
(4) sterilizing and drying the high-concentration solution obtained in step (3) to obtain a coarse powder; and
(5) superfinely grinding the coarse powder obtained in step (4) and sieving same to obtain a finished product, namely the micromolecular type III collagen peptide, wherein In step (1), preferably, the livestock and poultry skin may be from one or more of cow skin, pig skin, chicken skin and rabbit skin, and preferably, one or more of skin of the livestock and poultry at the age within 180 days.

In step (1), the mass ratio of the material to water in the first water washing and the second water washing is 1:(4-5); tap water is used for the first water washing; and purified water is used for the second water washing and stirring is performed during the second water washing.

In step (1), the mass fraction of the sodium chloride solution is 1%-2% and the soaking time of the sodium chloride solution is 1-2 h; and the mass fraction of the sodium hydroxide solution is 2%-3% and the soaking time of the sodium hydroxide solution is 2-3 h.

In step (1), the pH value is 6-7 and the electrical conductivity is 230-260 μs/cm.

Preferably, the pH value is adjusted by using hydrochloric acid, such as 5%-10% by mass of the hydrochloric acid.

In step (1), the pretreatment of livestock and poultry skin may further include removing skin hair on the head and legs by shaving or depilating, and cutting the skin into blocks. Preferably, the livestock and poultry skin is physically unhaired by blanching or electric shaving.

Preferably, the blocks may be 1-3 cm×1-3 cm and more preferably may be 2 cm×2 cm.

Preferably, in step (1), the temperature of the tap water for the first water washing is 15-25° C., so as to wash away foreign matters attached to the surface of the livestock and poultry skin raw material, and the washing is preferably performed for 1-3 times until washing clean; and the second water washing is performed for 3-8 time, so as to wash away attachments in the soaking process, and the second water washing is generally performed in a stirring manner, such as by using a stirring motor, wherein the stirring time is controlled within 5-15 min and the frequency of the stirring motor may be 20-30 Hz.

Preferably, in step (1), the mass ratio of the material to water in the first water washing is 1:4; and the mass ratio of the material to water in the second water washing is 1:5.

Specifically, in step (2),
the combined enzyme consists of the following enzymes:
a protease derived from *Bacillus licheniformis*, a protease derived from *Bacillus subtilis* and a protease derived from *Aspergillus niger*.

Preferably, the protease derived from *Bacillus licheniformis* is an alkaline protease; the protease derived from *Bacillus subtilis* is an alkaline protease or a neutral protease; and the protease derived from *Aspergillus niger* is a flavourzyme.

Preferably, the weight ratio of the protease derived from *Bacillus licheniformis*, the protease derived from *Bacillus subtilis* and the protease derived from *Aspergillus niger* is (20-80):(60-80):(1.5-3).

Further preferably, the weight ratio of the protease derived from *Bacillus licheniformis*, the protease derived from *Bacillus subtilis* and the protease derived from *Aspergillus niger* is 20:60:1.5.

Preferably, the addition amount of the combined enzyme is 0.815%-1.615% by weight of the livestock and poultry skin.

Further preferably, the addition amount of the combined enzyme is 0.815% by weight of the livestock and poultry skin.

Specifically, the enzymatic hydrolysis is performed at the pH of 6-8 and 50-60° C. for 2-4 h, and the temperature is raised to 80-85° C., maintained for 10-15 min and lowered to 50-55° C.

In some specific examples, step (2) may include:
conveying the material (pretreated livestock and poultry skin) in step (1) to an extraction tank, adding 5 times of low-temperature purified water (<20° C.), then the temperature is raised to 70-80° C. and maintained for 20-40 min, a plate-type heat exchanger is cooled to 50-60° C., the pH value is adjusted to 6-8, the protease derived from *Bacillus licheniformis*, the protease derived from *Bacillus subtilis* and the protease derived from *Aspergillus niger* are respectively added, and after enzymatic hydrolysis, the enzymatic hydrolysate is filtered by a filter sieve to remove residual hair and impurities.

The filter sieve may include:
a triangular screen: an upper gap of 1-3 mm and a lower gap of 0.1-0.5 mm; and a 60-80 mesh square vibrating sieve.

Specifically, in step (3),
the decolorization may be performed by using activated carbon and the activated carbon contains 3%-5% of the dry weight of solid matters.

The filtration is performed by using a rotary cross-flow membrane.

Preferably, the cross-flow filtering membrane used in the filtration is 20-50 nm, preferably 30 nm; and the filtering pressure is 0.2-0.3 MPa, preferably 0.2 Mpa. The filtered solution is clear and transparent.

The water exchange of solid matters use water at 50-70° C.

The nanofiltration aims to remove a sodium ion, preferably by using a KOCH nanofiltration membrane and the molecular weight cut-off of the KOCH nanofiltration membrane is 80-100 KDa. The nanofiltration pressure is 1.2-1.3 MPa.

The high-concentration solution is a transparent high-concentration type III collagen peptide solution with the solid matters of 30%-35%. The electrical conductivity of the 5% solid matters is 450-560 μs/cm.

Specifically, in step (4),
the intensive pulsed light sterilization and vacuum belt drying are performed.

The flow rate of the intensive pulsed light sterilization is 600-800 L/h and flash irradiation is performed for 50-60 times at 15-20 J once.

The vacuum belt drying is performed at the vacuum degree of −0.1 MPa.

The vacuum belt drying may use three-stage heating, for example, the temperature of a stage I is 70-80° C., the temperature of a stage II is 60-70° C. and the temperature of a stage III is 40-60° C. The feeding speed may be 700-800 L/h, the diameter of a spray gun nozzle may be 1.6-2.0 mm and the total heating time may be 60-80 min, so as to finally obtain the coarse powder with the water content of 5%-7%, for example, the coarse powder with the water content of 5.8%-6.3%. The vacuum belt drying further may include sieving, for example by using a 10-20 mesh screen in the machine.

Specifically, in step (5),
A cooling medium of the superfine grinding is at −10° C. to 0° C. and the grinding is performed for 10-120 min, preferably 10-15 min.

The sieving is performed by using a 50-300 mesh screen, preferably a 50-80 mesh screen.

For the range values of the conditions in the preparation method, those skilled in the art know that any combination of the methods can achieve the technical solution of the present disclosure and achieve the same technical effects. Those skilled in the art can prepare the corresponding products according to any combination of the above conditions.

At the same time, the present disclosure sets forth a micromolecular type III collagen peptide prepared by the preparation method.

In another aspect, the present disclosure provides a micromolecular type III collagen peptide.

The micromolecular type III collagen peptide comprises a specific peptide fragment.

Specifically, the micromolecular type III collagen peptide comprises any one or more of amino acid sequences shown in SEQ ID NOs. 1-8.

The micromolecular type III collagen peptide may include any 1, 2, 3, 4, 5, 6, 7 or 8 of the amino acid sequences shown in SEQ ID NOs. 1-8.

Preferably, the polypeptide comprises any one of the following:
(1) SEQ ID NOs. 1-7;
(2) SEQ ID NO. 4 and SEQ ID NO. 8;
(3) SEQ ID NO. 2 and SEQ ID NO. 4;
(4) SEQ ID NO. 4; and
(5) SEQ ID NO. 2, SEQ ID NO. 3, SEQ ID NO. 8 and SEQ ID NO. 6.

In another aspect, the present disclosure provides application of the micromolecular type III collagen peptide in the preparation of an oral collagen peptide product.

The oral collagen peptide product further may include other types of collagen peptides, for example, type I collagen peptide and/or type I collagen peptide.

The oral collagen peptide product may further include other common auxiliary materials in food or health-care products or medicines, including but not limited to an excipient, a flavoring agent, a toner, an acid-base balancing agent, a thickener and the like.

At the same time, the present disclosure comprises an oral collagen peptide product containing the micromolecular type III collagen peptide.

Beneficial effects of the present disclosure:

(1) The production period is short and the resulting product has good color and smell, high recovery rate, high content of the micromolecular type III collagen peptide and a specific sequence.

(2) The rotary cross-flow membrane is used for filtration and purification for the first time, so as to improve that the purity, the recovery rate, the brightness and the thermal stability of the product.

(3) The intensive pulsed light sterilization is used for the first time to replace membrane filtration sterilization and high-temperature sterilization, so as to ensure the sense and the activity of the product.

(4) Compared with the traditional spray drying, the vacuum low-temperature belt drying used for the first time to prepare the type III collagen peptide reduces the highest heating temperature of the product, consumes only one third of energy of the spray drying, has 10 times or more of the freezing capacity and consumes only one fourth of the energy of a freeze drying. Besides, during the whole feeding process, the product is in a low-temperature state of 0-5° C. so as to ensure the product activity.

(5) The product is crushed again by using superfine grinding for the first time to reach the effect of easy absorption.

DETAILED DESCRIPTION OF THE EMBODIMENTS

Figure 1:
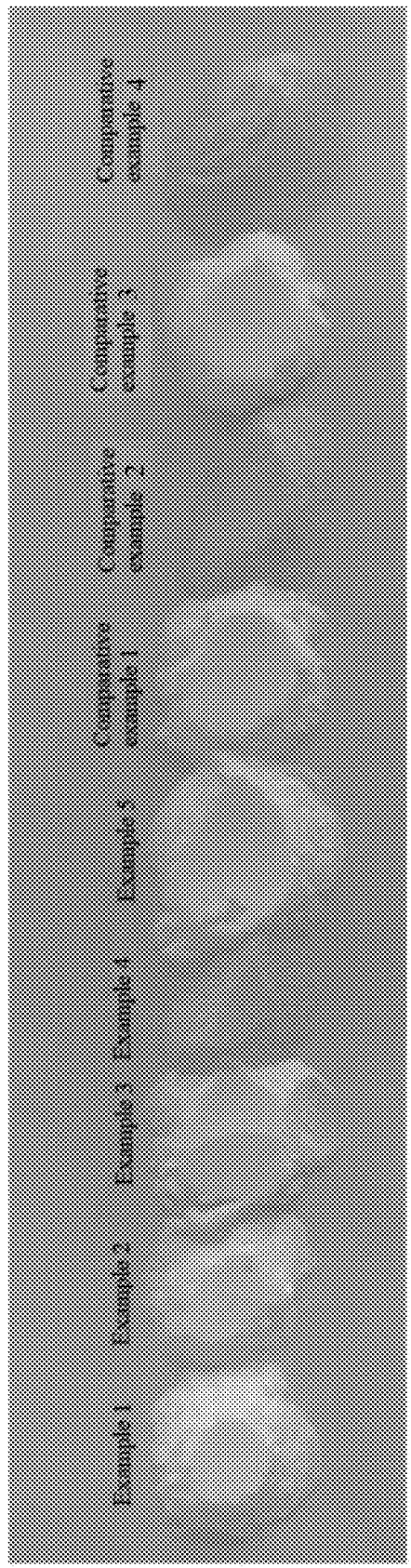
FIG. 1 is a photograph showing a comparison of sensory colors of products in examples and comparative examples.

The present disclosure is further described in detail below with reference to examples. The following examples are not used to limit the present disclosure, and only used to illustrate the present disclosure. The experiment methods used in the following examples are conventional, unless otherwise specified; the experimental methods in the examples without specified conditions are generally conducted under conventional conditions; and the used materials, agents, etc. in the examples are generally commercially available, unless otherwise specified.

Example 1

1. 1,000 kg of skin with hairs of rabbits freshly slaughtered for 70 days (purchased in a domestic formal slaughterhouse), the heads and legs were removed, the hairs were shaved with an industrial shaver, and the unhaired skin was cut into 2 cm×2 cm small blocks by using a slitter and dicer. The material (the original unhaired skin) was washed once by using 25° C. tap water at the ratio of the material (kg) to the water (kg) of 1:4, then the material was soaked by using a sodium chloride solution with the mass concentration of 1.5% at 25° C. for 1.5 h at the ratio of the material (kg) to the saline solution (kg) of 1:4, the water was drained, the material was soaked by using a sodium hydroxide solution with the mass concentration of 2% at 25° C. for 3 h at the ratio of the material (kg) to the sodium hydroxide solution (kg) of 1:4, and then the material was washed 5 times with purified water with stirring for 10 min each time and the frequency of a stirring motor of 20 HZ at the ratio of the material (kg) to the water (kg) of 1:5. The pH value was adjusted with a food-grade hydrochloric acid with the mass concentration of 6% during the washing process, the electrical conductivity is 260 μs/cm after the washing was finished, and the pH value of the washing water is 6.53.

2. The material obtained in step I was conveyed into an extraction tank, 4 times of low-temperature purified water was added, the temperature was raised to 80° C. and maintained for 30 min, a plate type heat exchanger was cooled to 55° C., and the pH value was adjusted to 6.8. A protease derived from *Bacillus licheniformis* (Novozymes, Alcalase, 2.4 L FG), a protease derived from *Bacillus subtilis* (Cangzhou Sunson Biotechnology Co., Ltd., FDG-2202, the enzyme activity ≥200,000 μ/g) and a protease derived from *Aspergillus niger* (Cangzhou Sunson Biotechnology Co., Ltd., FDG-2251, the enzyme activity ≥5,000 μ/g) were respectively added at the addition amount of 0.2%, 0.6% and 0.015% by weight of the unhaired rabbit skin for enzymatic hydrolysis for 2 h. Then the temperature was raised to 80° C., maintained for 15 min and lowered to 55° C. The residual hairs and impurities were filtered out through a triangular filter sieve (an upper gap of 2 mm and a lower gap of 0.5 mm of a triangular screen) and an 80-mesh square vibrating sieve. A clear liquid flew into a next working procedure.

3. Activated carbon with 3% of the dry weight of solid matters was added into the clear liquid for decoloring for 40 min. Then the clear liquid passed through a 30-nm cross-flow filtration membrane with the filtration pressure of 0.2 MPa. A clear and transparent type III collagen peptide solution was obtained after the filtration. A filtered concentrate was replaced with water at the temperature of 60° C. until the content of the solid matters was 0. The filtered material passed through a secondary KOCH nanofiltration membrane with the molecular weight cut-off of 100 Da to remove sodium ions and obtain a transparent high-concentration type III collagen peptide solution with the mass concentration of the solid matters of 35% (at this time, the electrical conductivity of 5% of the solid matters is 450 μs/cm) at the pressure of the nanofiltration process of 1.2 MPa.

4. The material in step 3 was fed into an intensive pulsed light sterilization device at the flow rate of 800 L/h and subjected to flash irradiation for 60 times at 20 J once. The material was conveyed to a storage tank and then to a vacuum belt dryer by using a screw pump at the vacuum degree of −0.1 Mpa. A three-stage heating was performed with the temperature of a stage I of 80° C., the temperature of a stage II of 60° C. and the temperature of a stage III of 40° C. The feeding speed was 800 L/h, the diameter of a spray gun nozzle was 2.0 mm, the total heating time was 60 min and an equipped grinder was provided with a 10-mesh screen, so as to finally obtain the coarse powder with the water content of 5.8%.

5. The coarse powder obtained in step 4 was ground again by using superfine grinding under a cooling medium of −10° C. to 0° C. for 15 min, and the powder passed through a 65-mesh screen to obtain a finished product.

The content and the polypeptide sequence of the finished product were detected, and the effect was verified.

Example 2

1. 1,000 kg of skin with hairs of calves freshly slaughtered for 120 days (purchased in a domestic formal slaughterhouse), the heads and legs were removed, the hairs were shaved with an industrial shaver, and the unhaired skin was cut into 2 cm×2 cm small blocks by using a slitter and a dicer. The material was washed once by using 20° C. tap water at the ratio of the material to the water of 1:4, then the material was soaked by using a sodium chloride solution with the mass concentration of 1.5% at 20° C. for 1.5 h at the ratio of the material to the saline solution of 1:4, the water was drained, the material was soaked by using a sodium hydroxide solution with the mass concentration of 2% at 20° C. for 3 h at the ratio of the material to the sodium hydroxide solution of 1:4, and then the material was washed 5 times with purified water with stirring for 10 min each time and the frequency of a stirring motor of 20 HZ at the ratio of the material to the water of 1:5. The pH value was adjusted with a food-grade citric acid with the mass concentration of 6% during the washing process, the electrical conductivity was 230 μs/cm after the washing was finished, and the pH value of the washing water was 6.38.

2. The material obtained in step 1 was conveyed into an extraction tank, 5 times of low-temperature purified water was added, the temperature was raised to 80° C. and maintained for 30 min, a plate type heat exchanger was cooled to 55° C., and the pH value was adjusted to 8.0. A commercially available protease derived from *Bacillus licheniformis*, a protease derived from *Bacillus subtilis* and a protease derived from *Aspergillus niger* were respectively added at the amounts of 0.4%, 0.6% and 0.015% by weight of the unhaired calf skin for enzymatic hydrolysis for 2 h. Then the temperature was raised to 80° C., maintained for 15 min and lowered to 55° C. The residual hairs and impurities were filtered out through a triangular filter sieve (an upper gap of 2 mm and a lower gap of 0.5 mm of a triangular screen) and an 80-mesh square vibrating sieve. A clear liquid flew into a next working procedure.

3. Activated carbon with 5% of the dry weight of solid matters was added into the clear liquid for decoloring for 40 min. Then the clear liquid passed through a 30-nm cross-flow filtration membrane with the filtration pressure of 0.2 MPa. A clear and transparent type III collagen peptide solution was obtained after the filtration. A filtered concentrate was exchanged with water at the temperature of 60° C. until the content of the solid matters was 0. The filtered material passed through a secondary KOCH nanofiltration membrane with the molecular weight cut-off of 100 Da to remove sodium ions and obtain a transparent high-concentration type III collagen peptide solution with the mass concentration of the solid matters of 30% (at this time, the electrical conductivity of 5% of the solid matters was 560 μs/cm) at the pressure of the nanofiltration process of 1.3 MPa.

4. The material in step 3 was fed into an intensive pulsed light sterilization device at the flow rate of 800 L/h and subjected to flash irradiation for 50 times at 15 J once. The material was conveyed to a storage tank and to a vacuum belt dryer by using a screw pump at the vacuum degree of −0.1 Mpa. A three-stage heating was performed with the temperature of a stage I of 80° C., the temperature of a stage II of 60° C. and the temperature of a stage III of 40° C. The feeding speed was 700 L/h, the diameter of a spray gun nozzle was 1.6 mm, the total heating time was 60 min and an equipped grinder was provided with a 10-mesh screen, so as to finally obtain the coarse powder with the water content of 6.3%.

5. The coarse powder obtained in step 4 was ground again by using superfine grinding under a cooling medium of −10° C. to 0° C. for 10 min, and the powder passed through a 50-mesh screen after the grinding to obtain a finished product.

Example 3

The steps of this example were the same as other steps of example 1 except that the raw material was adjusted to suckling pig skin and an enzyme preparation in step 2 was adjusted: the material obtained in step 1 was conveyed into an extraction tank, 5 times of low-temperature purified water was added, the temperature was raised to 80° C. and maintained for 30 min, a plate type heat exchanger was cooled to 55° C., and the pH value was adjusted to 6.0. A commercially available protease derived from *Bacillus licheniformis*, a protease derived from *Bacillus subtilis* and a protease derived from *Aspergillus niger* were respectively added at the amounts of 0.6%, 0.6% and 0.015% by weight of the unhaired suckling pig skin for enzymatic hydrolysis for 3 h. Then the temperature was raised to 80° C., maintained for 15 min and lowered to 55° C. The residual hairs and impurities were filtered out through a triangular filter sieve (an upper gap of 2 mm and a lower gap of 0.5 mm of a triangular screen) and an 80-mesh square vibrating sieve. A clear liquid flew into a next working procedure.

Example 4

The steps of this example were the same as other steps of example 1 except that the raw material was adjusted to chicken skin and an enzyme preparation in step 2 was adjusted: the material obtained in step 1 was conveyed into an extraction tank, 5 times of low-temperature purified water was added, the temperature was raised to 80° C. and maintained for 30 min, a plate type heat exchanger was cooled to 55° C., and the pH value was adjusted to 7.5. A commercially available protease derived from *Bacillus licheniformis*, a protease derived from *Bacillus subtilis* and a protease derived from *Aspergillus niger* were respectively added at the amounts of 0.8%, 0.8% and 0.015% by weight of the unhaired chicken skin for enzymatic hydrolysis for 4 h. Then the temperature was raised to 80° C., maintained for 15 min and lowered to 55° C. The residual hairs and impurities were filtered out through a triangular filter sieve (an upper gap of 2 mm and a lower gap of 0.5 mm of a triangular screen) and an 80-mesh square vibrating sieve. A clear liquid flew into a next working procedure.

Example 5

The steps of this example were the same as other steps of example 1 except that an enzyme preparation in step 2 was adjusted: the material obtained in step 1 was conveyed into an extraction tank, 5 times of low-temperature purified water was added, the temperature was raised to 80° C. and maintained for 30 min, a plate type heat exchanger was cooled to 55° C., and the pH value was adjusted to 6.0. A commercially available protease derived from *Bacillus licheniformis*, a protease derived from *Bacillus subtilis* and a protease derived from *Aspergillus oryzae* were respectively added at the amounts of 0.8%, 0.8% and 0.03% by weight of the unhaired rabbit skin for enzymatic hydrolysis for 4 h. Then the temperature was raised to 80° C., maintained for 15 min and lowered to 55° C. The residual hairs and impurities were filtered out through a triangular filter sieve (an upper gap of 2 mm and a lower gap of 0.5 mm of a triangular screen) and an 80-mesh square vibrating sieve. A clear liquid flew into a next working procedure.

Comparative Example 1

All the steps were the same as those in example 2 except that the raw material was changed to skin of 18-month-old cows purchased from a formal slaughterhouse.

Comparative Example 2

All the steps were the same as those in example 3 except that the raw material was changed to skin of 12-month-old pigs purchased from a formal slaughterhouse.

Comparative Example 3

The steps 1, 2 and 3 were the same as those in example 1. In step 4, a high-pressure pulse sterilization was also used, then panning was performed for freeze drying with a cold trap at −45° C. by using a freeze dryer with the volume of 40 m² for 36 h. 240 kg of powder was discharged. The production efficiency was only one thirtieth of that of vacuum belt drying and spray drying, and thus the production was not feasible.

Comparative Example 4

Compared with example 1, in step 1, only shaving and dicing, and water washing were performed, and other steps were the same.

Experimental Example 1 Detection of Molecular Weight

The products obtained in all the examples and comparative examples were tested for average molecular weight and for the proportion of relative molecular weight <10,000 u by using the method of GB/T 22729. The detection results were shown in Table 1.

TABLE 1

Average molecular weight and peak area percentage (%, λ220 nm) for different molecular weight ranges

| Molecular weight range | Example 1 | Example 2 | Example 3 | Example 4 | Example 5 | Comparative example 1 | Comparative example 2 | Comparative example 3 | Comparative example 4 |
|---|---|---|---|---|---|---|---|---|---|
| >10,000 | 3.67 | 0.42 | 0.16 | 0.05 | 0 | 1.44 | 0.41 | 1.24 | 2.07 |
| 5,000-10,000 | 6.8 | 1.92 | 1.51 | 1.0 | 0.18 | 3.95 | 2.41 | 10.64 | 10.03 |
| 3,000-5,000 | 9.67 | 5.35 | 4.98 | 3.58 | 1.73 | 7.81 | 7.06 | 14.78 | 15.56 |
| 2,000-3,000 | 11.14 | 7.34 | 7.51 | 6.23 | 3.84 | 9.28 | 9.12 | 13.67 | 14.28 |
| 1,000-2,000 | 20.11 | 18.78 | 18.81 | 18.58 | 15.97 | 19.65 | 20.81 | 24.9 | 23.78 |
| 500-1,000 | 24.12 | 29.07 | 29.44 | 31.83 | 33.32 | 25.71 | 30.41 | 21.47 | 20.02 |
| <500 | 24.49 | 37.12 | 37.58 | 38.73 | 44.96 | 32.15 | 29.78 | 13.30 | 14.26 |
| Average molecular weight | 2,141 | 1,141 | 1,071 | 964 | 764 | 1,571 | 1,303 | 2,324 | 2,433 |
| Percentage (%) of relative molecular weight less than 10,000 u | 96.33 | 99.58 | 99.84 | 99.95 | 100 | 98.56 | 99.59 | 98.76 | 97.93 |

Experimental Example 2 Detection of Sense

The sensory test method was as follows:

Color: 3 g of the products were respectively taken and put on white paper to observe colors.

Taste: the products were dissolved to 20% by using purified water at 50° C. for tasting.

Smell: method I: the products were smelled directly by opening self-sealing bags; and method II: 20 g of powder was poured to 80 g of at 50° C. and smelled instantly.

The sensory colors were compared in FIG. 1. In combination with FIG. 1, the results of taste and smell were described in Table 2.

TABLE 2

Description of results of taste and smell

| Product No. | Odor | Taste | Color |
| --- | --- | --- | --- |
| Example 1 | No peculiar smell | Slightly sweet | White |
| Example 2 | Calf meat smell | Slightly bitter | Milk white |
| Example 3 | Slightly burnt and meat smell | Obviously bitter | Milk white |
| Example 4 | Meat smell and burnt smell | Obviously bitter | Dark yellow |
| Example 5 | No peculiar smell | Bitter | Milk white |
| Comparative example 1 | Calf meat smell | Slightly bitter | Milk white |
| Comparative example 2 | Obviously burnt and slightly meat smell | Obviously bitter | Dark yellow |
| Comparative example 3 | Slightly meat smell | Slightly sweet | Milk white |
| Comparative example 4 | Meat smell and oil-rancidity smell | Obvious oil-rancidity smell and meat smell | Dark yellow |

Experimental Example 3 Acid-Resistant High-Temperature Experiment

Acid-resistant high-temperature experiment: 36 g of the products, 36 g of purified water and 1.5 g of citric acid were heat-preserved at 85° C. for 40 min to observe whether the solution had a precipitate or not so as to ensure that the products can be used in an oral liquid.

Figure 2:
FIG. 2 is a photograph comparing acid-resistant high-temperature experiments of the products in examples and comparative examples.
Figure 3:
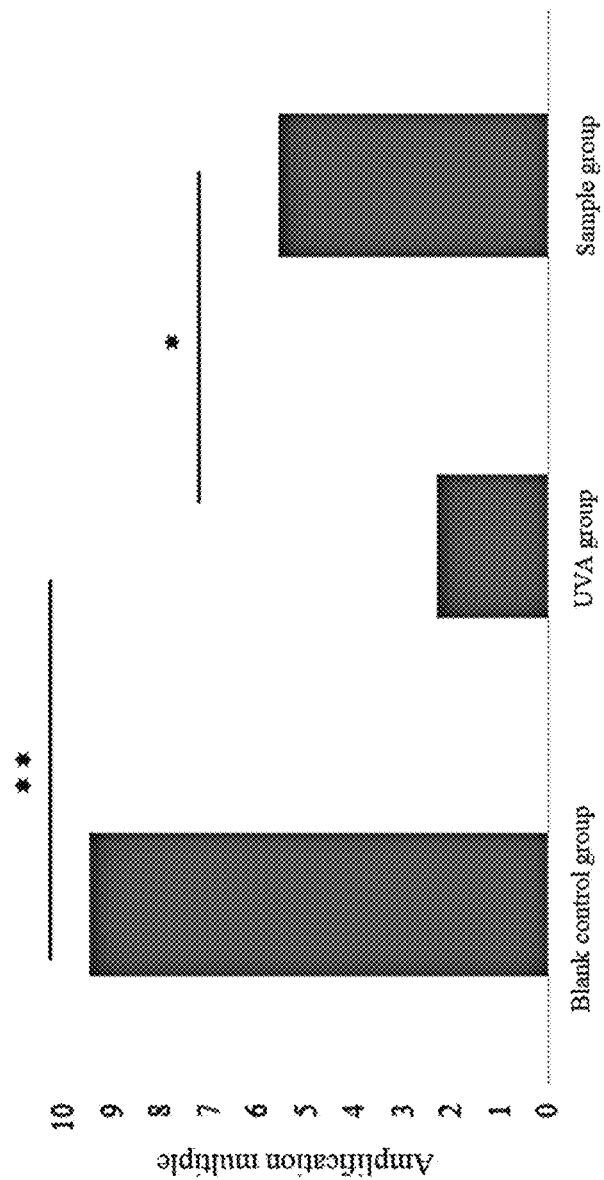
FIG. 3 shows the relative expression amount of a hyaluronic acid gene in human skin fibroblasts in experimental example 5.
Figure 4:
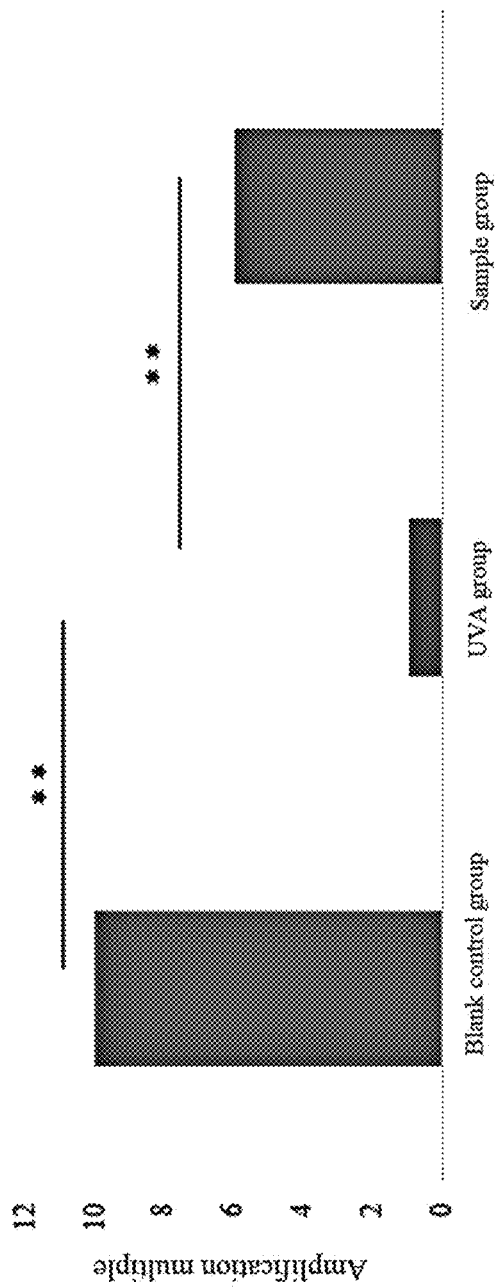
FIG. 4 shows the relative expression amount of a type I collagen gene in the human skin fibroblasts in experimental example 5.
Figure 5:
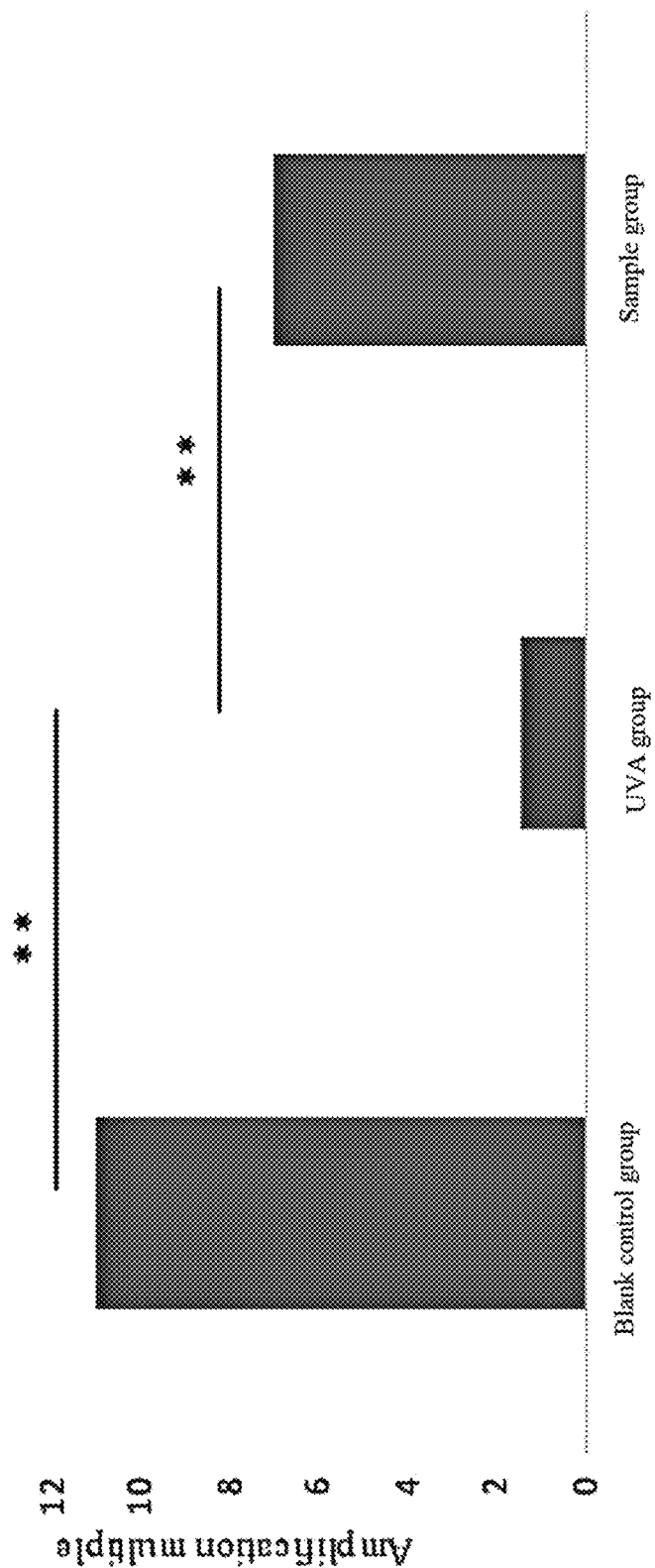
FIG. 5 shows the relative expression amount of a type III collagen gene in the human skin fibroblasts in experimental example 5.
Figure 6:
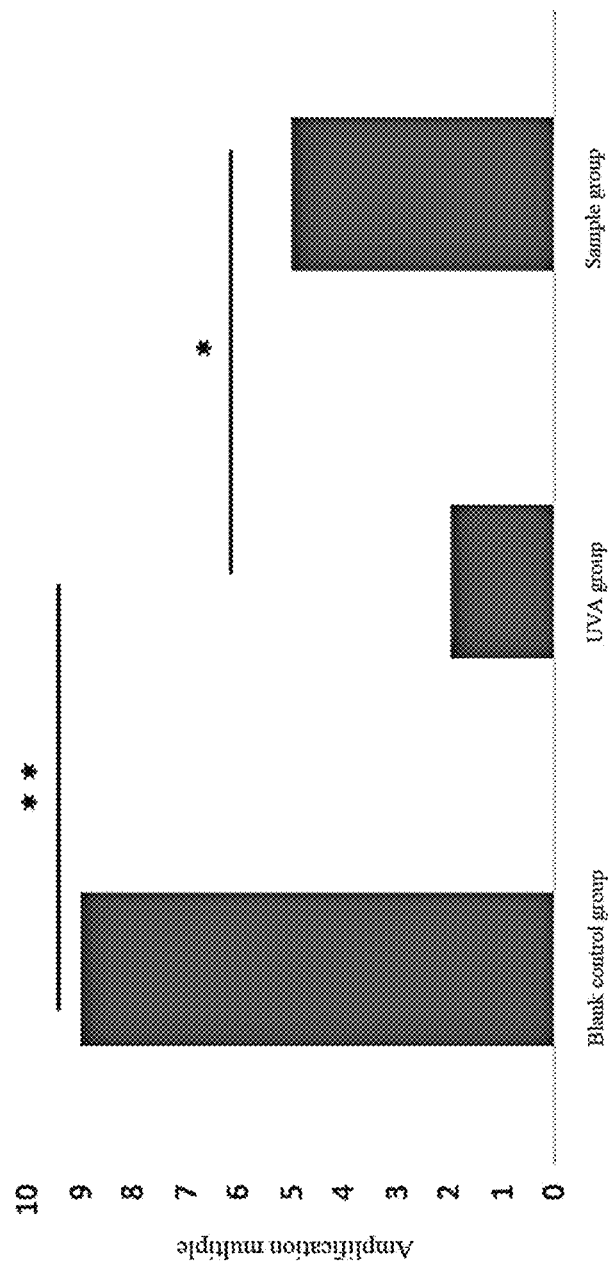
FIG. 6 shows the relative expression amount of a type I collagenV gene in the human skin fibroblasts in experimental example 5.

The comparison of the acid-resistant high-temperature experiments was shown in FIG. 2 (9 pictures were taken). The products of examples 1-5 and comparative examples 1-4 respectively corresponded to the order of test tubes from left to right in the pictures.

From the experimental results, it can be seen that the products of examples 1-5 were all transparent, but the products with smaller molecular weight were darker in color after heated. Since the product in comparative example 4 was pretreated, the turbidity appeared in the high-temperature high-acid experiment, and thus the product is not suitable for being prepared into an oral liquid. No precipitate appeared in comparative examples 1, 2 and 3, indicating that the pretreatment had great influence on the high-temperature high-acid stability of the material.

Experimental Example 4 Qualitative Test

A qualitative test method for a type III collagen peptide sequence:

A liquid chromatography-mass spectrometry consisted of Vanquish liquid chromatography of Thermo Fisher company in America and Orbitrap Exploris 480 mass spectrometry. A data acquisition and processing software was Xcalibur4.4.

Chromatographic condition: chromatographic column: Peptide BEH C18 130 Å; mobile phase: A-water (0.1% formic acid); and B-60% acetonitrile (0.1% formic acid); gradient: 0-60 min, 5-40% B; 60-85 min, 40-90% B; 85-98 min, 90% B; 98-100 min, 90%-5% B; 100-110 min, 5% B; flow rate: 0.2 mL/min; column temperature: 60° C.; and injection volume: 5 μL. Mass spectrometry condition: ESI ionization; spray voltage: 4.5 kV; shell airflow rate: 60 arb (about 400 kPa); scanning range (m/z): 400-2,000; positive ion monitoring mode; secondary mass spectrometry scan (MS/MS): data-dependent scan; and secondary mass spectrometry collision energy: 35%.

The detection results were shown in Table 3:

TABLE 3

| Product No. | Sequence of contained characteristic peptide |
| --- | --- |
| Example 1 | SEQ ID NO. 1: GQpGDKGEGGApGVpGIAGPR; |
| | SEQ ID NO. 2: GERGEAGSpGIAGPK; |
| | SEQ ID NO. 3: GERGGpGGpGPQGPAGKN; |
| | SEQ ID NO. 4: GEAGSpGIAGPK; |
| | SEQ ID NO. 5: GEGGApGVpGIAGPR; |
| | SEQ ID NO. 6: GENGIpGENGApGPMGPR; |
| | SEQ ID NO. 7: GPAGANGLPGEKGppGER; |
| Example 2 | SEQ ID NO. 4: GEAGSpGIAGPK; |
| | SEQ ID NO. 8: GEGGApGVpGIAGPR; |
| Example 3 | SEQ ID NO. 2: GERGEAGSpGIAGPK; |
| | SEQ ID NO. 4: GEAGSpGIAGPK; |
| Example 4 | SEQ ID NO. 4: GEAGSpGIAGPK; |
| Example 5 | SEQ ID NO. 2: GERGEAGSpGIAGPK; |
| | SEQ ID NO. 3: GERGGpGGpGPQGPAGKN; |
| | SEQ ID NO. 8: GEGGApGVpGIAGPR; |
| | SEQ ID NO. 6: GENGIpGENGApGPMGPR; |
| Comparative example 1 | None |
| Comparative example 2 | None |
| Comparative example 3 | SEQ ID NO. 1: GQpGDKGEGGApGVpGIAGPR; |
| | SEQ ID NO. 2: GERGEAGSpGIAGPK; |
| | SEQ ID NO. 8: GEGGApGVpGIAGPR; |
| | SEQ ID NO. 7: GPAGANGLPGEKGppGER; |
| Comparative example 4 | SEQ ID NO. 2: GERGEAGSpGIAGPK; |
| | SEQ ID NO. 4: GEAGSpGIAGPK; |
| | SEQ ID NO. 7: GPAGANGLPGEKGppGER; |

Note: p represented hydroxyproline.

From the above example, it can be seen that:

the molecular weights of the products in all the cases were concentrated between 500-3,000 Da. The proportions of the relative molecular weights of all the products less than 10,000 u all reached 95% or more.

In all the examples, type III characteristic peptides were detected, but the product in example 1 contained more type III characteristic peptide fragment, and had the most pleasant taste and the highest recovery rate.

The type III characteristic peptide was not detected in comparative examples 1 and 2, indicating selectivity of a production raw material containing the type III peptide.

The product in comparative example 3 had good color and taste, may also contain four type III characteristic peptide fragments. However, since the production efficiency of freeze drying was too low, the production cost was hundreds of times of that of examples.

Although the type III characteristic peptides were detected in comparative example 4, the product had poor color, taste and smell, and is difficult to take. Besides, turbidity generated in the high-temperature experiment. Therefore, the product cannot be used for oral liquid production and also did not have commercial value.

In summary, the optimal formula was example 1. Therefore, the product obtained in example 1 was used for a subsequent efficacy experiment.

Example 5 Fluorescent Quantitative PCR Detection of Expressions of Related Genes of Hyaluronan Synthase 3, Type I Collagen, Type III Collagen and Type I CollagenV in Human Skin Fibroblasts Fibroblast cells (Guangdong BioCell Biotechnology Co. Ltd.) were respectively inoculated into 6-well plates and transferred into an incubator (37° C. and 5% $CO_2$) to be incubated for 24 h. When the plating rate of the cells reached to 50%-60%, the medium was changed and the sample was added. 2 mL of the samples was added per well with 3 multiple wells per group. The cells were placed in the incubator (37° C. and 5% $CO_2$) to be incubated for 24 h.

The related gene detection was performed by setting a blank control group, a UVA group and a sample group (1.0 mg/mL of a type III collagen peptide). Except the blank control group (normal cells, not subjected to UVA irradiation nor added with any ingredients), the other groups were both subjected to the UVA irradiation at the irradiation dose of 30 $J/cm^2$. After the irradiation, the cells were placed in the incubator (37° C. and 5% $CO_2$) to be continuously cultured for 24 h. Each well was washed twice with 2 mL of PBS, 1 mL of RNAiso Plus (TaKaRa, Japan, Article No. 9108) was added, the cells were lysed by pipetting and the sample was collected. According to the instructions of a kit (TaKaRa, Japan, Article No. RR036A), RNA extraction, reverse transcription and fluorescent quantitative PCR were performed to detect the expression amounts of the related genes (type I collagen, type III collagen and type I collagenV). The information for detection primers was as follows:

| Gene | Sequence (5'→ 3') |
|---|---|
| type I collagen | F: CCCTCCCACAACTCTGACAT (SEQ ID NO. 9) |
|  | R: AGGGAATCGCGTTTATAGGGT (SEQ ID NO. 10) |
| type III collagen | F: TGGTCTGCAAGGAATGCCTGGA (SEQ ID NO. 11) |
|  | R: TCTTTCCCTGGGACACCATCAG (SEQ ID NO. 12) |
| type I collagen V | F: TCCAGGGTTTCCAGGCGACTC (SEQ ID NO. 13) |
|  | R: GGTCCCGTGCCAATAACAGTTCC (SEQ ID NO. 14) |
| Hyaluronan synthase 3 | F: CTTAAGGGTTGCTTGCTTGC (SEQ ID NO. 15) |
|  | R: GTTCGTGGGAGATGAAGGAA (SEQ ID NO. 16) |

Experimental Results and Analysis the results of the expression experiment of the related genes of the human skin fibroblasts were shown in FIGS. 3-6.

The results indicated that the type III collagen peptide had obvious effects of promoting the expressions of the genes such as hyaluronan synthase, type I collagen, type III collagen and type I collagenV in the human skin fibroblasts injured by UVA.

What is claimed is:

1. A method for preparing a micromolecular type III collagen peptide, comprising the following steps:

step (1), pretreating livestock and poultry skin, sequentially comprising: first water washing, sodium chloride solution soaking, sodium hydroxide solution soaking and second water washing, wherein the pH value and the electrical conductivity in the second water washing are adjusted;

step (2), enzymatically hydrolyzing the livestock and poultry skin treated in step (1) by using a combined enzyme, and filtering an enzymatic hydrolysate to obtain a clear liquid;

step (3), decoloring and filtering the clear liquid obtained in step (2), exchanging water until the solid matters is 0, and performing nanofiltration to obtain a high-concentration solution;

step (4), sterilizing and drying the high-concentration solution obtained in step (3) to obtain a coarse powder; and step (5), superfinely grinding the coarse powder obtained in step (4) and sieving same to obtain a finished product, namely the micromolecular type III collagen peptide, wherein in step (1), the livestock and poultry skin is from livestock and poultry at the age within 180 days; and the livestock and poultry skin is selected from rabbit skin, pig skin, cow skin or chicken skin;

in step (1), the mass ratio of the material to water in the first water washing and the second water washing is 1: (4-5); tap water is used for the first water washing; and purified water is used for the second water washing and stirring is performed during the second water washing;

in step (1), the mass fraction of the sodium chloride solution is 1%-2% and the soaking time of the sodium chloride solution is 1-2 h; and the mass fraction of the sodium hydroxide solution is 2%-3% and the soaking time of the sodium hydroxide solution is 2-3 h;

in step (1), the pH value is 6-7 and the electrical conductivity is 230-260 μs/cm;

in step (3), the high-concentration solution is a solution with the solid matters of 30%-35%;

in step (2), the combined enzyme consists of the following enzymes: a protease derived from *Bacillus licheniformis*, a protease derived from *Bacillus subtilis* and a protease derived from *Aspergillus niger*; the weight ratio of the protease derived from *Bacillus licheniforˍ*

*mis*, the protease derived from *Bacillus subtilis* and the protease derived from *Aspergillus niger* is (20-80):(60-80):(1.5-3);

in step (2), the addition amount of the combined enzyme is 0.815%-1.615% by weight of the livestock and poultry skin; and the enzymatic hydrolysis is performed at the pH of 6-8 and 50-60° C. for 2-4 h, and the temperature is raised to 80-85° C., maintained for 10-15 min and lowered to 50-55° C.; and wherein the micromolecular type III collagen peptide comprises SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

2. The preparation method according to claim 1, wherein the pretreatment of livestock and poultry skin further comprises removing skin hair on the head and legs by shaving or depilating, and cutting the skin into blocks.

3. The preparation method according to claim 2, wherein the weight ratio of the protease derived from *Bacillus licheniformis*, the protease derived from *Bacillus subtilis* and the protease derived from *Aspergillus niger* is 20:60:1.5.

4. The preparation method according to claim 1, wherein in step (3), the decolorization is performed by using activated carbon and the activated carbon contains 3%-5% of the dry weight of solid matters; and the filtration is performed by using a rotary cross-flow membrane; the cross-flow filtering membrane used in the filtration is 20-50 nm; the filtering pressure is 0.2-0.3 MPa; a water exchange of solid matters uses water at 50-70° C.; and the nanofiltration uses a nanofiltration membrane, the molecular weight cut-off of the nanofiltration membrane is 80-100 KDa and the nanofiltration pressure is 1.2-1.3 MPa.

5. The preparation method according to claim 1, wherein in step (4), the intensive pulsed light sterilization and vacuum belt drying are performed.

6. The preparation method according to claim 5, wherein in step (4), the flow rate of the intensive pulsed light sterilization is 600-800 L/h and flash irradiation is performed for 50-60 times at 15-20 J once; and the vacuum belt drying is performed at the vacuum degree of −0.1 MPa, three-stage heating is used with total heating time of 60-80 min, wherein the three-stage heating is performed as follows: the temperature of a stage I is 70-80° C., the temperature of a stage II is 60-70° C. and the temperature of a stage III is 40-60° C. the feeding speed is 700-800 L/h, the diameter of a spray gun nozzle is 1.6-2.0 mm, so as to finally obtain the coarse powder with the water content of 5%-7%.

* * * * *